United States Patent [19]
Conrow et al.

[11] 4,387,059
[45] Jun. 7, 1983

[54] UREYLENEBIS SUBSTITUTED (OR UNSUBSTITUTED) PHENYLENE-CARBONYL (OR SULFONYL)-IMINO-1,3,5 OR 6-NAPHTHALENE-TRISULFONIC ACIDS AND SALTS

[75] Inventors: Ransom B. Conrow, Pearl River; John F. Poletto, Nanuet; Seymour Bernstein, New City, all of N.Y.

[73] Assignee: American Cyanamid Company, Stamford, Conn.

[21] Appl. No.: 324,749

[22] Filed: Nov. 25, 1981

[51] Int. Cl.$^3$ .................. C07C 143/30; C07D 241/06; C07D 213/20

[52] U.S. Cl. .................. 260/506; 260/501.19; 260/501.21; 260/507 R; 260/510; 544/410; 546/347; 546/184; 424/315; 424/316; 424/250; 424/267

[58] Field of Search .............. 260/506, 501.19, 501.21; 544/410; 546/347, 184

[56] References Cited

U.S. PATENT DOCUMENTS

| | | | |
|---|---|---|---|
| 4,147,801 | 4/1979 | Lenhard et al. | 260/506 |
| 4,155,930 | 5/1979 | Sinta et al. | 260/506 |
| 4,185,032 | 1/1980 | Sinta et al.a | 260/506 |

*Primary Examiner*—Nicky Chan
*Attorney, Agent, or Firm*—Anne M. Rosenblum

[57] ABSTRACT

Ureylenebis substituted (or unsubstituted) phenylene-carbonyl (or sulfonyl)-imino-1,3,5 or 6-naphthalenetrisulfonic acids and salts thereof, useful as complement inhibitors, the intermediates thereof, and the process of making such intermediates and end products.

3 Claims, No Drawings

UREYLENEBIS SUBSTITUTED (OR UNSUBSTITUTED) PHENYLENE-CARBONYL (OR SULFONYL)-IMINO-1,3,5 OR 6-NAPHTHALENE-TRISULFONIC ACIDS AND SALTS

BACKGROUND OF THE INVENTION

1. Field of the Invention

The present invention relates to novel ureylenebis substituted (or unsubstituted) phenylenecarbonyl (or sulfonyl)-imino-1,3,5 or 6-naphthalenetrisulfonic acids and salts thereof, to their use as inhibitors of the complement system of warm-blooded animals, and to the intermediates thereof. The invention further concerns a process for making such compounds.

2. Description of the Prior Art

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 20 proteins in the complement system consisting of the so-called classical and alternative pathways. These complement proteins are generally designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its biochemical, biological and pathological role in the body processes can be found in, for example, Bull. W.H.O. 39: 935 (1968); Annu. Rev. Med. 19: 1 (1968); Johns Hopkins Med. J. 128: 57 (1971); Harvey Lect. 66: 75 (1972); N. Engl. J. Med. 287: 452, 489, 454, 592, 642 (1972); Sci. Am. 229 (5): 54 (1973); Fed. Proc. 32: 134 (1973): Med. World, Oct. 11, 1974, p. 53; J. Allergy Clin. Immunol. 53: 298 (1974); Cold Spring Harbor Conf. Cell Proliferation 2/Proteases Biol. Control: 229 (1975); Annu. Rev. Biochem. 44: 697 (1975); Complement in Clinical Medicine, Dis. Mon. (1975); Complement, Scope, December 1975; Ann. Intern. Med. 84: 580 (1976); Transplant Rev.: 32 (1976); "Complement: Mechanisms and Functions," Prentice-Hall, Englewood Cliffs, N.J. (1976); Essays Med. Biochem. 2: 1 (1976); Hosp. Pract. 12: 33 (1977); Perturbation of Complement in Disease, Chap. 15 in Biol. Amplification Systems in Immunol. (Ed. Day and Good), Plenum, New York and London (1977); Am. J. Clin. Pathol. 68: 647 (1977); Biochem. Soc. Trans. 5: 1659 (1977); Harvey Lect. 72: 139 (1976-1977); J. Periodontol. 48: 505 (1977); Biochem. Soc. Trans. 6: 798 (1978); Clin. and Exp. Dermatol. 4: 271 (1979): Infect. Dis. Rev. 1: 483 (1979).

The complement system (e.g., classical pathway) can be considered to consist of three subsystems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is nonspecific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to host's cells. Immunity is, therefore, a double-edge sword.

Activation of the complement system also accelerates blood clotting. This action comes about by way of the complement-mediated release of a clotting factor from platelets. The biologically active complement fragments and complexes become involved in reactions that damage the host's cells. These pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain complement proteins, suggestion regarding the mode of complement binding to biological membranes and the manner in which complement effects membrane damage are discussed in Annu. Rev. Biochem. 38: 389 (1969); J. Exp. Med. 141: 724 (1975); J. Immunol. 116: 1431 (1976); 119: 1, 1195, 1358, 1482 (1977); 120: 1841 (1978); Immunochemistry 15: 813 (1978); J. Biol. Chem. 254: 9908 (1979).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anti-complementary effect, Br. J. Exp. Pathol. 33: 327 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, J. Med. Chem. 12: 415, 902, 1049, 1053 (1969); Can. J. Biochem. 47: 547 (1969); J. Immunol. 104: 279 (1970); J. Immunol. 106: 241 (1971); J. Immunol. 111: 1061 (1973); Biochim. Biophys. Acta 317: 539 (1973); Life Sci. 13: 351 (1973);

J. Immunol. 113: 584 (1974); Immunology 26: 819 (1974); J. Med. Chem. 17: 1160 (1974); Biochim. Biophys. Res. Comm. 67: 225 (1975); Ann. N.Y. Acad. Sci. 256: 441 (1975); J. Med. Chem. 19: 634, 1079 (1976); J. Immunol. 118: 466 (1977); Arch. Int. Pharmacodyn. 226: 281 (1977); Biochem. Pharmacol. 26: 325 (1977); J. Pharm. Sci. 66: 1367 (1977); Chem. Pharm. Bull. 25: 1202 (1977); Biochim. Biophys. Acta 484: 417 (1977); J. Clin. Microbiol. 5: 278 (1977); Immunochemistry 15: 231 (1978); Immunology 34: 509 (1978); J. Exp. Med. 147: 409 (1978); Thromb. Res. 14: 179 (1979); J. Immunol. 122: 2418 (1979); J. Chem. Soc. Chem. Comm. 726 (1979); Immunology 36: 131 (1979); Biochim. Biophys. Acta 611: 196 (1980); and J. Med. Chem. 23:240 (1980).

It has been reported that the known complement inhibitors, epsilon-aminocaproic acid and tranexamic acid, have been used with success in the treatment of hereditary angioneurotic edema, a disease state resulting from an inherited deficiency or lack of function of the serum inhibitor of the activated first component of complement (C1 inhibitor), N. Engl. J. Med. 286: 808 (1972); 287: 452 (1972); Ann. Intern. Med. 84: 580 (1976); J. Allergy Clin. Immunol. 60: 38 (1977). Also androgenic steroids have been used successfully in the treatment of this physiological disorder; see Medicine 58: 321 (1979); Arthritis Rheum. 22: 1295 (1979); Am. J. Med. 66: 681 (1979); and J. Allergy Clin. Immunol. 65: 75 (1980).

It has also been reported that the drug pentosanpolysulfoester has an anticomplementary activity on human serum, both in vitro and in vivo, as judged by the reduction in total hemolytic complement activity, Pathol. Biol. 25: 33; 25 (2): 105; 25 (3): 179 (1977).

SUMMARY OF THE INVENTION

It has now been discovered that certain ureylenebis substituted (or unsubstituted) phenylenecarbonyl (or sulfonyl)-imino-1,3,5 or 6-naphthalenetrisulfonic acids and salts interact with the complement reaction sequence, thereby inhibiting complement activity in body fluids.

This invention also concerns a method of inhibiting the complement system in a body fluid which comprises subjecting body fluid complement to the action of an effective complement inhibiting amount of the above-identified compounds. This invention further deals with a method of inhibiting the complement system in a warm-blooded animal which comprises administering to said animal an effective complement inhibiting amount of the above described compounds.

DETAILED DESCRIPTION OF THE INVENTION

In accordance with the present invention, there are provided novel compounds represented by the following generic formula:

FORMULA I

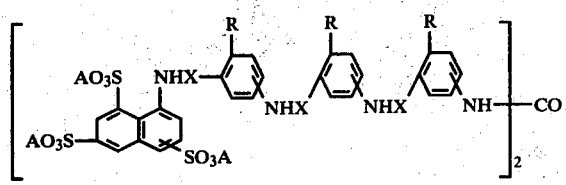

wherein X is selected from the group consisting of —CO— and —SO$_2$—; R is selected from the group consisting of hydrogen and —SO$_3$A; and A is selected from the group consisting of hydrogen and a nontoxic pharmaceutically acceptable salt cation, wherein the salt forming moiety is selected from the group consisting of alkali metal, alkaline earth metal, ammonia and substituted ammonia selected from the group consisting of trialkylamine (C$_1$–C$_6$), piperidine, pyrazine, alkanolamine (C$_2$–C$_6$) and cycloalkylamine (C$_3$–C$_6$).

Particularly preferred compounds of this invention which are of major interest as complement inhibitors include the following:

8,8'-Ureylenebis[tris[(2-sulfo-p-phenylenecarbonyl)imino]]-di-1,3,6-naphthalenetrisulfonic acid, dodecasodium salt 8,8'-[Ureylenebis[[[[[[(m-phenylenesulfonyl)imino]-m-phenylene]sulfonyl]imino]-m-phenylene]sulfonyl]imino]]-1,3,6-naphthalenetrisulfonic acid, hexasodium salt.

Other representative compounds with complement inhibiting activity encompassed within Formula I are, for example:

8,8'-Ureylenebis[tris[(2-sulfo-p-phenylenecarbonyl)imino]]-di-1,3,5-naphthalenetrisulfonic acid, dodecasodium salt 8,8'-[Ureylenebis[[[[[[(m-phenylenesulfonyl)imino]-m-phenylene]sulfonyl]imino]-m-phenylene]sulfonyl]imino]]-1,3,5-naphthalenetrisulfonic acid, hexasodium salt.

This invention further deals with a method of inhibiting the complement system in a body fluid, such as blood serum, which comprises subjecting body fluid complement to the action of an effective complement inhibiting amount of a compound of the above formula. Body fluids can include blood, plasma, serum, synovial fluid, cerebrospinal fluid, or pathological accumulations of fluid such as pleural effusion, etc. This invention also concerns a method of inhibiting the complement system in a warm-blooded animal which comprises administering to said warm-blooded animal an effective complement inhibiting amount of a compound of the above formula.

The above compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. These compounds may also be used in the therapeutic treatment of warm-blooded animals having non-immunologic diseases such as paroxysmal nocturnal hemoglobinurea, hereditary angioneurotic edema (such as Suramin Sodium, etc.) and inflammatory states induced by the action of bacterial or lysosomal enzymes on the appropriate complement components as, for example, inflammation following coronary occulsion. They may also be useful in the treatment of transplant rejection and ulcers and as blood culture and transport mediums. The compounds of this invention such as the sodium and aluminum salts may be particularly useful in the treatment of ulcers and the like on oral therapy.

In addition, this invention is concerned with compounds of the following Formula II that are useful as intermediates in the preparation of the compounds of Formula I:

FORMULA II

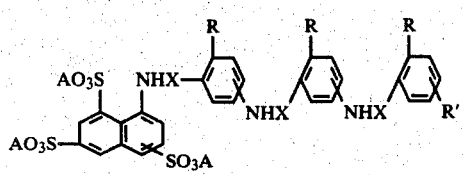

wherein x, A and R are as described for Formula I and R' is selected from the group consisting of —NO$_2$ and —NH$_2$.

Representative compounds encompassed within the above Formula II include, for example:

8-[4-[4-(4-Nitro-2-sulfobenzamido)-2-sulfobenzamido]-2-sulfobenzamido]-1,3,6-naphthalenetrisulfonic acid, hexasodium salt 8-[4-[4-(4-Amino-2-sulfobenzamido)-2-sulfobenzamido]-2-sulfobenzamido]-1,3,6-naphthalenetrisulfonic acid, hexasodium salt 8-[N$^3$-[N-(m-Nitrophenylsulfonyl)metanilyl]metanilamino]-1,3,6-naphthalenetrisulfonic acid, trisodium salt 8-[N$^4$-(N-Metanilylmetanilyl)metanilamino]-1,3,6-naphthalenetrisulfonic acid, trisodium salt.

The compounds of the present invention may be prepared according to the following flowchart.

FLOWCHART

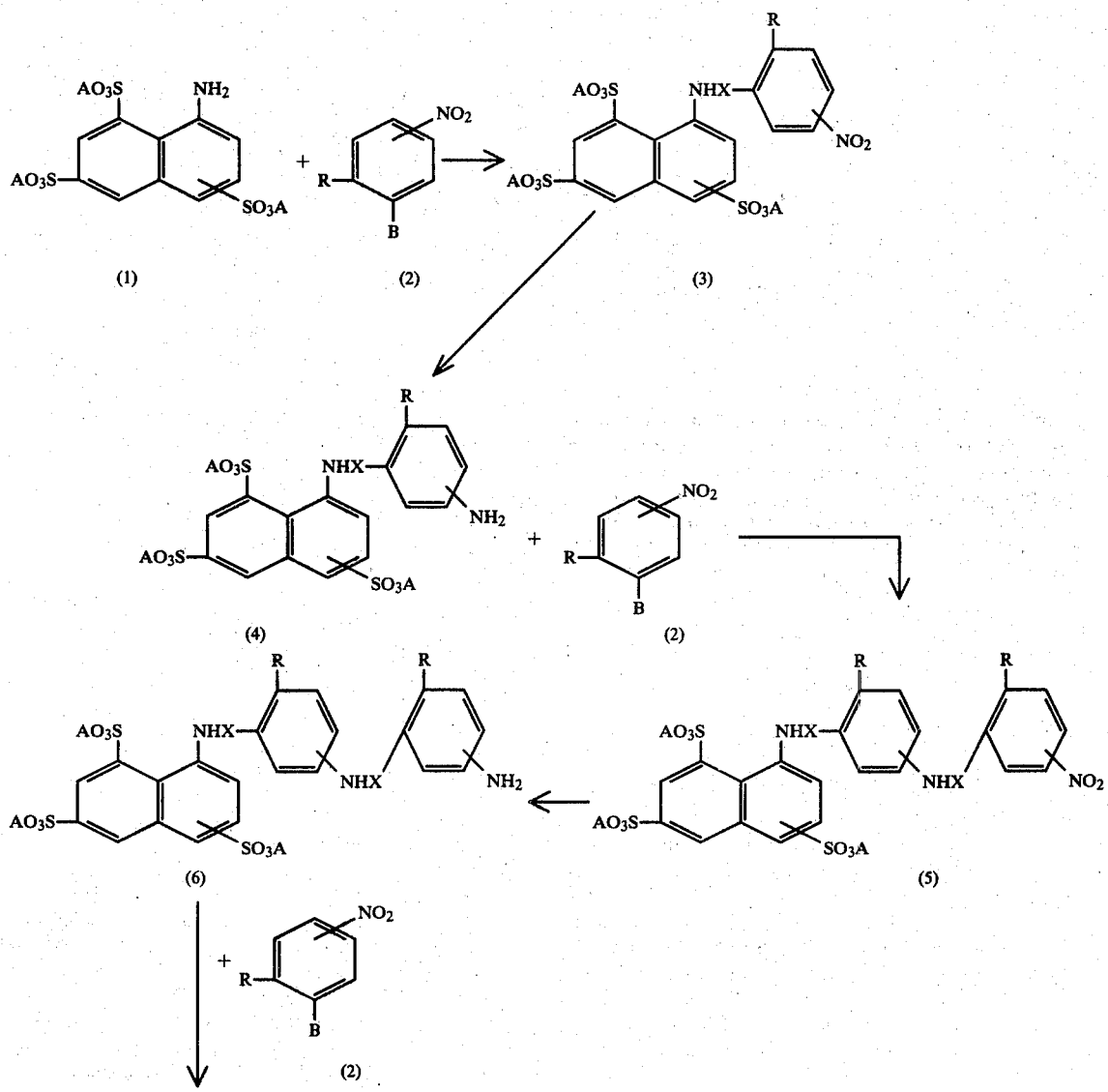

-continued
FLOWCHART

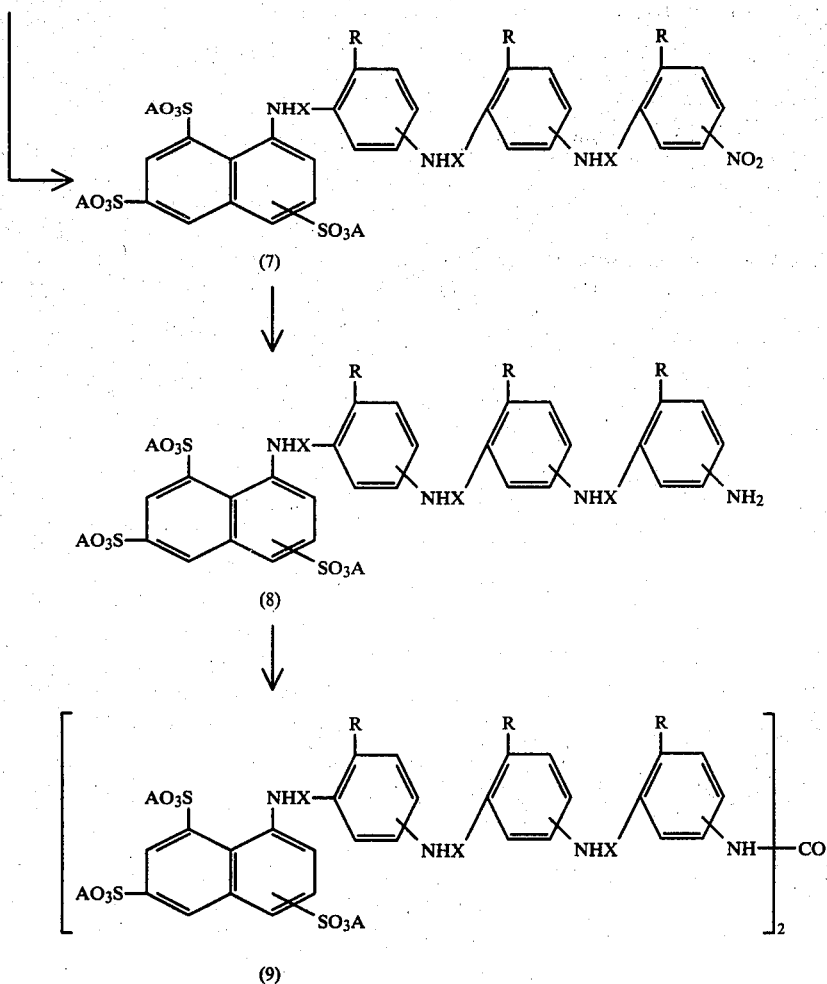

With reference to the preceding flowchart, an aqueous solution of an 8-amino-1,3,5 or 6-naphthalenetrisulfonic acid or salt (1), where A is hydrogen or a pharmaceutically acceptable salt cation as previously described and sodium acetate or sodium carbonate, is treated with either m-nitrobenzenesulfonyl chloride or 4-nitro-2-sulfobenzoic anhydride (2), where R is hydrogen or —SO$_3$A and B is —SO$_2$Cl or

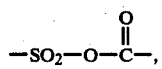

by stirring for several hours. The resulting naphthalenetrisulfonic acid salt (3), where A and R are as previously described and X is —SO$_2$— or —CO—, is isolated by precipitation with ethanol. The nitro derivative (3) is catalytically reduced to the corresponding amine (4). The amine (4) is then reacted with (2) as described above, to produce the nitro derivative (5). Catalytic reduction gives the corresponding amine (6). Reaction of (6) with (2) gives the nitro derivative (7) and subsequent reduction produces the amine (8) which is the immediate precursor to the final products (9). The amine precursor (8) in aqueous solution with pyridine is phosgenated and the resulting products (9) are isolated by extraction from ethanol.

It is generally preferred that the respective product of each process step, described hereinabove, is separated and/or isolated prior to its use as starting material for subsequent steps. Separation and isolation can be effected by any suitable purification procedure such as, for example, evaporation, crystallization, column chromatography, thin-layer chromatography, distillation, etc. Also, it should be appreciated that when typical reaction conditions (e.g., temperatures, mole ratios, reaction times) have been given, the conditions which are both above and below these specified ranges can also be used, though generally less conveniently.

The term "pharmaceutically acceptable salts" refers to those salts of the parent compound which do not significantly or adversely affect the pharmaceutical properties (e.g. toxicity, effectiveness, etc.) of the parent compound. The salt forming moiety of the present invention which is pharmaceutically acceptable includes the alkali metals (e.g., sodium, potassium, etc.); alkaline earth metals (e.g., calcium, etc.); ammonia; and substituted ammonia selected from the group consisting of trialkylamine (C$_1$–C$_6$), piperidine, pyrazine, alkanolamine (C$_2$–C$_6$) and cycloalkylamine (C$_3$–C$_6$).

The term "trialkylamine (C$_1$–C$_6$)" defines those amines having three aliphatic fully saturated hydrocarbon substituents containing 1 to 6 carbon atoms either linearly or branched. Typically, these amines are trimethylamine, triethylamine, tripropylamine, dimethylamine, dimethyl-1-propylamine, etc. The term "alkanolamine ($C_2$–$C_6$)" refers to the above-defined trialkylamines additionally substituted with at least one and not more than three hydroxy groups on at least two of the alkyl hydrocarbon chains. Such amines are, for example, triethanolamine, tripropanolamine, etc. The term "cycloalkylamine ($C_3$–$C_6$)" is defined as the 3 to 6 fully saturated carbocyclic moieties such as cyclopropyl, methylcyclobutyl, cyclopentyl, cyclohexyl, etc.

As used hereinabove and below unless expressly stated to the contrary, all temperatures and temperature ranges refer to the centigrade system and the terms "ambient" or "room temperature" refer to about 25° C. The term "percent" or "(%)" refers to weight percent and the terms "mole" and "moles" refer to gram moles. The term "equivalent" refers to a quantity of reagent equal in moles to the moles of the preceding or succeeding reactant recited in the Preparation or Example in the term of moles of finite weight or volume.

Whereas the exact scope of the instant invention is set forth in the appended claims, the following specific examples illustrate certain aspects of the present invention. However, the examples are set forth for illustration only and are not to be construed as limitations on the present invention except as set forth in the appended claims.

A further understanding of the invention can be obtained from the following non-limiting Preparations and Examples.

EXAMPLE 1

8-[4-[4-(4-Nitro-2-sulfobenzamido)-2-sulfobenzamido]-2-sulfobenzamido]-1,3,6-naphthalenetrisulfonic acid, hexasodium salt A solution of 100 g of 5-nitro-o-toluenesulfonic acid in a mixture of 600 ml of water and 80 ml of 5 N sodium hydroxide was heated to 90° C. A 240 g portion of potassium permanganate was added portionwise to maintain reflux over a 1¼ hour period. The mixture was filtered and the residue was washed with water. The combined filtrate and wash was concentrated in vacuo to about 300 ml, then warmed on a steam bath. The solution was cooled to room temperature and the precipitate was collected by filtration, washed with ice water and then ethanol. The filtrate was concentrated further to 150 ml giving a second precipitate. The total crude yield was 86.2 g. This crude product was heated with 220 ml of water, cooled slightly to 80° C. and filtered. The filtrate was cooled to room temperature and refiltered. This filtrate was concentrated in steps providing a total of 71.3 g of purified product. This product was dissolved in 250 ml of water containing 35 ml of concentrated hydrochloric acid on a steam bath, then diluted with 300 ml of ethanol and allowed to crystallize at room temperature. The mixture was stored in a cold room for two days, then filtered and washed with cold 50% aqueous ethanol, then ethanol and finally ether. The solid was recrystallized from 200 ml of boiling water by cooling in an ice bath. The product was dried overnight at 110° C. giving 52.0 g of 4-nitro-2-sulfobenzoic acid-2-sodium salt.

A mixture of 50.0 g of 4-nitro-2-sulfobenzoic acid-2-sodium salt and 500 g of thionyl chloride was stirred and refluxed for 19 hours, filtered and evaporated in vacuo to dryness. The residue was warmed with 300 ml of toluene and filtered. The filtrate was evaporated in vacuo to about 200 ml, warmed to produce solution and then cooled in an ice bath. The solid was collected by filtration, washed with hexane and evaporated in vacuo giving white crystals. These crystals were recrystallized from 175 ml of toluene with ice bath cooling, giving 30.4 g of 4-nitro-2-sulfobenzoic anhydride as a solid, m.p. 110°–116° C.

A solution of 51.2 g of 8-amino-1,3,6-naphthalenetrisulfonic acid disodium salt in a mixture of 120 ml of water and 21.0 ml of 5 N sodium hydroxide was warmed and then filtered. The filtrate was slowly diluted with 400 ml of ethanol. The mixture was cooled to room temperature and the solid was collected by filtration, washed with ethanol, then ether and dried at 110° C. overnight giving 46.0 g of 8-amino-1,3,6-naphthalenetrisulfonic acid, trisodium salt.

To a solution of 32.0 g of 8-amino-1,3,6-naphthalenetrisulfonic acid, trisodium salt and 15.0 g of sodium acetate trihydrate in 200 ml of water at 2° C. (ice bath) was added 19.25 g of 4-nitro-2-sulfobenzoic anhydride. The solution was stirred in the ice bath for 10 minutes and then filtered. The filtrate was cooled in an ice bath, acidified with 6 ml of concentrated hydrochloric acid and diluted with one liter of cold (5° C.) ethanol. The solid was collected by filtration and washed with 240 ml of 83.5% aqueous ethanol, ethanol and then ether giving 42.4 g of 8-(4-nitro-2-sulfobenzamido)-1,3,6-naphthalenetrisulfonic acid, tetrasodium salt.

A mixture of 42.4 g of 8-(4-nitro-2-sulfobenzamido)-1,3,6-naphthalenetrisulfonic acid, tetrasodium salt, and 1.5 g of 10% palladium-on-carbon in 150 ml of water was hydrogenated in a Parr shaker for one hour. The mixture was filtered through diatomaceous earth. The filtrate was concentrated to about 130 ml and poured with vigorous stirring into 500 ml of absolute ethanol. The resulting gum was collected by filtration through diatomaceous earth and then dissolved from the diatomaceous earth with water. The aqueous solution was concentrated to 15 ml and then diluted with 85 ml of ethanol giving a gum which was stirred with absolute ethanol giving a solid which was dried overnight in a pistol at 110° C. giving 36.15 g of 8-(4-amino-2-sulfobenzamido)-1,3,6-naphthalenetrisulfonic acid, tetrasodium salt.

To an ice-cold solution of 17.2 g of 8-(4-amino-2-sulfobenzamido)-1,3,6-naphthalenetrisulfonic acid, tetrasodium salt, and 5.24 g of sodium acetate trihydrate in 100 ml of water was added 6.87 g of 4-nitro-2-sulfobenzoic anhydride. The mixture was stirred for 10 minutes, and filtered through diatomaceous earth. The filtrate was poured into 750 ml of absolute ethanol with vigorous stirring and cooled in an ice bath. The solid was recovered by filtration, washed with ethanol and ether and evaporated in vacuo overnight. This solid was dissolved in 100 ml of water, acidified with 3 ml of concentrated hydrochloric acid, and then poured with vigorous stirring into 500 ml of cold absolute ethanol. The solid was collected by filtration, washed with ethanol, then ether, and dried overnight at 110° C., giving 19.35 g of 8-[4-(4-nitro-2-sulfobenzamido)-2-sulfobenzamido]-1,3,6-naphthalenetrisulfonic acid, pentasodium salt as a powder.

A reaction mixture comprising 17.5 g of 8-[4-(4-nitro-2-sulfobenzamido)-2-sulfobenzamido]-1,3,6-naphthalenetrisulfonic acid, pentasodium salt, 1.0 g of 10% palladium on carbon catalyst and 100 ml of water was hydrogenated in a Parr shaker for one hour and then filtered through diatomaceous earth. The filtrate was concentrated to about 65 ml and then poured with vigorous stirring into 500 ml of absolute ethanol. The granular precipitate was collected by filtration, washed with ethanol, then ether and dried for three days at 110° C., giving 8-[4-(4-amino-2-sulfobenzamido)-2-sulfobenzamido]-1,3,6-naphthalenetrisulfonic acid, pentasodium salt.

To a solution of 5.03 g of 8-[4-(4-amino-2-sulfobenzamido)-2-sulfobenzamido]-1,3,6-naphthalenetrisulfonic acid, pentasodium salt, and 1.05 g of sodium acetate trihydrate in 20 ml of water at 2° C. in an ice bath was added 1.37 g of 4-nitro-2-sulfobenzoic anhydride. The mixture was stirred for 10 minutes in the ice bath and then filtered. The filtrate was poured into 150 ml of absolute ethanol cooled in an ice bath. The resulting solid was collected by filtration, washed with ethanol and ether, then dissolved in 20 ml of water and acidified with 1.0 ml of concentrated hydrochloric acid. This solution was poured into 100 ml of ethanol. The solid was collected by filtration, washed with ethanol and ether and then dissolved in 20 ml of water. This solution was gradually diluted with 50 ml of ethanol at room temperature, then mixed and heated on a steam bath producing a yellow solid. The mixture was cooled to room temperature and the solid was collected by filtration, washed with 71.5% ethanol, then ethanol and finally ether and dried overnight at 110° C. giving 3.07 g of the desired final product as a powder.

EXAMPLE 2

8-[4-[4-(4-Amino-2-sulfobenzamido)-2-sulfobenzamido]-2-sulfobenzamido]-1,3,6-naphthalenetrisulfonic acid, hexasodium salt A mixture comprising 11.61 g of the end product of Example 1, 1.0 g of 10% palladium-on-carbon catalyst and 75 ml of water was hydrogenated on a Parr shaker for 1.5 hours and then filtered through diatomaceous earth. The filtrate was concentrated to about 50 ml and poured into 400 ml of absolute ethanol with rapid stirring. The mixture was heated to boiling then cooled to room temperature. The solid was collected by filtration, washed with ethanol, then ether and dried overnight at 110° C. giving 11.14 g of the desired product as a powder.

EXAMPLE 3

8,8'-Ureylenebis[tris[(2-sulfo-p-phenylenecarbonyl)imino]]-di-1,3,6-naphthalenetrisulfonic acid, dodecasodium salt Phosgene was passed into a cooled solution of 4.45 g of the end product of Example 2, 3.5 ml of pyridine and 25 ml of water until it was acidic. A 0.5 ml portion of pyridine was added to neutralize the solution which was then poured into 250 ml of ethanol. The resulting precipitate was collected by filtration, washed with ethanol and then dissolved in 15 ml of water. This solution was neutralized by the addition of 5 N sodium hydroxide, heated on a steam bath and gradually diluted with 20 ml of ethanol. The mixture was cooled to room temperature and diluted further with 130 ml of ethanol. The solid was collected by filtration, washed with ethanol, then ether and dried overnight at 110° C., giving 4.35 g of the desired product as a powder.

EXAMPLE 4

8-[$N^3$-[N-(m-Nitrophenylsulfonyl)metanilyl]metanilamido]-1,3,6-naphthalenetrisulfonic acid, trisodium salt To a solution of 21.9 g of 8-amino-1,3,6-naphthalenetrisulfonic acid, trisodium salt and 11.4 g of sodium carbonate in 280 ml of water was added 24 g of m-nitrobenzenesulfonyl chloride. The mixture was stirred overnight at room temperature, concentrated, dissolved in 200 ml of water and flooded with absolute ethanol. The solid was collected by filtration, washed with ethanol, then ether and evaporated in vacuo at 75° C., giving 26.1 g of 8-[$N^3$-(m-nitrophenylsulfonyl)]-1,3,6-naphthalenetrisulfonic acid, trisodium salt.

A 26.1 g portion of the above nitro derivative and 2.09 g of 10% palladium-on-carbon catalyst in 175 ml of water was hydrogenated in a Parr shaker. The mixture was filtered, the filtrate was evaporated and then dissolved in 60 ml of water. A 400 ml portion of absolute ethanol was added and the mixture was stirred for several hours. The solid was collected by filtration, washed with ethanol and ether and dried, giving 25.3 g of 8-[$N^3$-(m-aminophenylsulfonyl)]-1,3,6-naphthalenetrisulfonic acid, trisodium salt.

An 11.26 g portion of the above amino derivative and 4.72 g of sodium carbonate were dissolved in 200 ml of water. A 10 g portion of m-nitrobenzenesulfonyl chloride was added and the mixture was stirred for 18 hours at room temperature. The mixture was filtered and the filtrate was flooded with ethanol and stirred for one hour. The solid was collected by filtration, washed with absolute ethanol, then ether and dried, giving 8.9 g of 8-[$N^3$-(m-nitrophenylsulfonyl)metanilamido]-1,3,6-naphthalenetrisulfonic acid, trisodium salt.

An 8.3 g portion of 8-[$N^3$-(m-nitrophenylsulfonyl)metanilamido]-1,3,6-naphthalenetrisulfonic acid, trisodium salt and 1.0 g of 10% palladium-on-carbon catalyst in 90 ml of water was hydrogenated on a Parr shaker. The mixture was filtered and the filtrate was concentrated, dissolved in 25 ml of water and precipitated by the addition of absolute ethanol. The solid was collected by filtration, washed with ethanol and ether and dried, giving 7 g of 8-[$N^3$-(m-aminophenylsulfonyl)metanilamido]-1,3,6-naphthalenetrisulfonic acid, trisodium salt.

A mixture of 7.0 g of 8-[$N^3$-(m-aminophenylsulfonyl)metanilamido]-1,3,6-naphthalenetrisulfonic acid, trisodium salt, 4.9 g of m-nitrobenzenesulfonyl chloride, 2.32 g of sodium carbonate and 140 ml of water was stirred overnight at room temperature, concentrated and filtered. The filtrate was evaporated to dryness, then dissolved in 30 ml of water and added to 600 ml of ethanol with stirring. The solid was recovered by filtration, washed with ethanol, then ether and then evaporated in vacuo at 75° C. giving 7.2 g of the desired product.

EXAMPLE 5

8-[$N^4$-N-Metanilylmetanilyl)metanilamido]-1,3,6-naphthalenetrisulfonic acid, trisodium salt A 7 g portion of the end product of Example 4, 1.0 g of 10% palladium-on-carbon catalyst and 80 ml of water was hydrogenated on a Parr shaker. The mixture was filtered, the filtrate was evaporated to dryness and then dissolved in water. Absolute ethanol was added and the solid was collected by filtration, washed with ethanol and ether and dried giving 4.2 g of the desired product.

EXAMPLE 6

8,8'-[Ureylenebis[[[[[[(m-phenylenesulfonyl)imino]-m-phenylene]sulfonyl]imino]-m-phenylene]sulfonyl]-imino]]-1,3,6-naphthalenetrisulfonic acid, hexasodium salt A mixture of 4.0 g of the end product of Example 5, 35 ml of water and 2.2 ml of pyridine was phosgenated with vigorous stirring until acid to Congo Red paper. A 1.1 ml portion of pyridine was added and the mixture was further phosgenated until acid to Congo Red paper. The mixture was neutralized with pyridine, poured into 400 ml of absolute ethanol, stirred for 1⁄8 hour and filtered. The solid was washed with ethanol and ether and dried, then dissolved in 30 ml of water, made basic (pH 8) with 5 N sodium hydroxide, neutralized with acetic acid and poured into 800 ml of absolute ethanol. The mixture was stirred ½ hour, concentrated to about 650 ml and allowed to cool with stirring. The mixture was concentrated to dryness, dissolved in 25 ml of water and added slowly to 400 ml of ethanol. The solid was collected by filtration, washed with ethanol, then ether and dried. This solution was dissolved in 30 ml of water, adjusted to pH 8-9 with 5 N sodium hydroxide, neutralized to pH 7 with acetic acid and filtered. The filtrate was slowly added to 400 ml of ethanol. The solid was collected by filtration, washed with ethanol, then ether and dried at 110° C. in a pistol, giving 1.6 g of the desired product.

EXAMPLE 7

Preparation of Compressed Tablet

| Ingredient | mg/Tablet |
|---|---|
| Active Compound | 0.5-500 |
| Dibasic Calcium Phosphate NF | qs |
| Starch USP | 40 |
| Modified Starch | 10 |
| Magnesium Stearate USP | 1-5 |

EXAMPLE 8

Preparation of Compressed Tablet-Sustained Action

| Ingredient | mg/Tablet |
|---|---|
| Active Compound as Aluminum Lake*, Micronized | 0.5-500 (as acid equivalent) |
| Dibasic Calcium Phosphate NF | qs |
| Alginic Acid | 20 |
| Starch USP | 35 |
| Magnesium Stearate USP | 1-10 |

*Complement inhibitor plus aluminum sulfate yields aluminum complement inhibitor. Complement inhibitor content in aluminum lake ranges from 5-30%.

EXAMPLE 9

Preparation of Hard Shell Capsule

| Ingredient | mg/Capsule |
|---|---|
| Active Compound | 0.5-500 |
| Lactose, Spray Dried | qs |
| Magnesium Stearate | 1-10 |

EXAMPLE 10

Preparation of Oral Liquid (Syrup)

| Ingredient | % W/V |
|---|---|
| Active Compound | 0.05-5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 11

Preparation of Oral Liquid (Elixir)

| Ingredient | % W/V |
|---|---|
| Active Compound | 0.05-5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 12

Preparation of Oral Suspension (Syrup)

| Ingredient | % W/V |
|---|---|
| Active Compound as Aluminum Lake, Micronized | 0.05-5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 13

Preparation of Injectable Solution

| Ingredient | % W/V |
|---|---|
| Active Compound | 0.05-5 |
| Benzyl Alcohol NF | 0.9 |
| Water for Injection | 100.0 |

EXAMPLE 14

Preparation of Injectable Oil

| Ingredient | % W/V |
|---|---|
| Active Compound | 0.05-5 |
| Benzyl Alcohol | 1.5 |
| Sesame Oil qs ad | 100.0 |

EXAMPLE 15

Preparation of Intra-Articular Product

| Ingredient | Amount |
|---|---|
| Active Compound | 2-20 mg |
| NaCl (physiological saline) | 0.9% |
| Benzyl Alcohol | 0.9% |

-continued

| Ingredient | Amount |
| --- | --- |
| Sodium Carboxymethylcellulose | 1.5% |
| pH adjusted to 5.0–7.5 | |
| Water for Injection qs ad | 100% |

EXAMPLE 16
Preparation of Injectable Depo Suspension

| Ingredient | % W/V |
| --- | --- |
| Active Compound | 0.05–5 |
| | (acid equivalent) |
| Polysorbate 80 USP | 0.2 |
| Polyethylene Glycol 4000 USP | 3.0 |
| Sodium Chloride USP | 0.8 |
| Benzyl Alcohol NF | 0.9 |
| HCl to pH 6–8 | qs |
| Water for Injection qs ad | 100.0 |

EXAMPLE 17
Preparation of Dental Paste

| Ingredient | % W/W |
| --- | --- |
| Active Compound | 0.05–5 |
| Zinc Oxide | 15 |
| Polyethylene Glycol 4000 USP | 50 |
| Distilled Water qs | 100 |

EXAMPLE 18
Preparation of Dental Ointment

| Ingredient | % W/W |
| --- | --- |
| Active Compound | 0.05–5 |
| Petrolatum, White USP qs | 100 |

EXAMPLE 19
Preparation of Dental Cream

| Ingredient | % W/W |
| --- | --- |
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 20
Preparation of Topical Cream

| Ingredient | % W/W |
| --- | --- |
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |

-continued

| Ingredient | % W/W |
| --- | --- |
| Purified Water qs | 100 |

EXAMPLE 21
Preparation of Topical Ointment

| Ingredient | % W/W |
| --- | --- |
| Active Compound | 0.05–5 |
| Cholesterol | 3 |
| Stearyl Alcohol | 3 |
| White Wax | 8 |
| Petrolatum, White USP qs | 100 |

EXAMPLE 22
Preparation of Spray Lotion (Non-aerosol)

| Ingredient | % W/W |
| --- | --- |
| Active Compound | 0.05–5 |
| Isopropyl Myristate | 20 |
| Alcohol (Denatured) qs | 100 |

EXAMPLE 23
Preparation of Buccal Tablet

| Ingredient | mg/Tablet |
| --- | --- |
| Active Ingredient | 3.25 |
| 6 × Sugar | 290.60 |
| Acacia | 14.53 |
| Soluble Starch | 14.53 |
| F. D. & C. Yellow No. 6 Dye | 0.49 |
| Magnesium Stearate | 1.60 |
| | 325.00 |

The final tablet will weigh about 325 mg and may be compressed into buccal tablets in flat faced or any other tooling shape convenient for buccal administration.

EXAMPLE 24
Preparation of Lozenge

| Ingredient | g/Lozenge |
| --- | --- |
| Active Ingredient | 0.0140 |
| Kompact ® Sugar (Sucrest Co.) | 0.7138 |
| 6 × Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝" flat based lozenge tooling. Other shapes may also be utilized.

The compounds of the present invention may be administered internally, e.g., orally, intra-articularly or parenterally, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate nontoxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term "dosage form," as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention is indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test Code 035 (C3–C9 inhibitor)—This test determines the ability of the late components of human complement (C3–C9) to lyse EAC 142 in the presence of appropriate dilutions of the test compound. An active inhibitor protects EAC 142 from lysis by human C3–C9; (iii) Test Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Cap 50 Test—Here, appropriate amounts of the test compound are added to a pool of guinea pig serum in vitro, after which the complement level is determined in undiluted serum by the serum capillary tube assay of U.S. Pat. No. 3,876,376. The concentration of compound inhibiting 50% is reported; and (v) Guinea Pig Intraperitoneal Test (GPIP)—Guinea pigs weighing about 300 g are dosed intraperitoneally (i.p.) with 200 mg/kg of the test compound dissolved in saline and adjusted to pH 7–8. Approximately 0.4 blood samples, taken by orbital sinus puncture 30 minutes and one hour after injections, are collected directly into centrifuge tubes; 5 ml blood samples, taken by decapitation 2 hours after injection, are collected directly into diSPo® beakers. The samples were allowed to clot, centrifuged, and the resultant sera were assayed for complement activity using the capilllary complement assay. Percent inhibition is calculated by comparison with simultaneous controls. The results of the GPIP appear in Table I together with results of Test Code 026, 035, 036 and Cap 50. Table I shows that the compounds of the invention possess highly significant complement inhibiting activity in warm-blooded animals.

TABLE I

| Compound | Biological Activity | | | | in vivo Activity (Guinea Pig) | | |
|---|---|---|---|---|---|---|---|
| | in vitro Activity | | | | % Inhibition Intravenous Time (Minutes) | | |
| | Cl 026* Wells | C-Late 035* Wells | C-Shunt Inhibition 036* Wells | Cap 50 | 2 | 30 | 120 |
| 8,8'-Ureylenebis[tris[(2-sulfo-p-phenylenecarbonyl)imino]]-di-1,3,6-naphthalenetrisulfonic acid, dodecasodium salt | +5** | +2 | | 158 | 95 | 54 | 14 |
| 8,8'-[Ureylenebis[[[[[[(m-phenylenesulfonyl)-imino]-m-phenylene]sulfonyl]imino]-m-phenylene]sulfonyl]imino]]-1,3,6-naphthalenetrisulfonic acid, hexasodium salt | +4 | +4 | +1 | >500 | | | |

*Tests identified by code herein.
**Activity in wells, a serial dilution assay; higher well number indicates higher activity. The serial dilutions are two-fold.

We claim:

1. A compound selected from those of the formula:

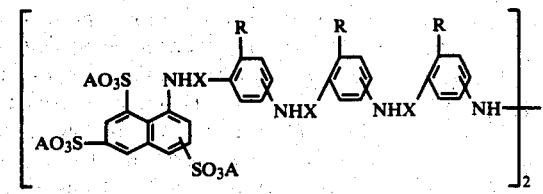

wherein X is selected from the group consisting of —CO— and —SO$_2$—; R is selected from the group consisting of hydrogen and —SO$_3$A; and A is selected from the group consisting of hydrogen and a nontoxic pharmaceutically acceptable salt cation, wherein the salt forming moiety is selected from the group consisting of alkali metal, alkaline earth metal, ammonia and substituted ammonia selected from the group consisting of trialkylamine (C$_1$-C$_6$), piperidine, pyrazine, alkanolamine (C$_2$-C$_6$) and cycloalkylamine (C$_3$-C$_6$).

2. The compound, 8,8'-ureylenebis[tris[(2-sulfo-p-phenylenecarbonyl)imino]]-di-1,3,6-naphthalenetrisulfonic acid, dodecasodium salt.

3. The compound, 8,8'-[ureylenebis[[[[[[(m-phenylenesulfonyl)imino]-m-phenylene]sulfonyl]imino]-m-phenylene]sulfonyl]imino]]-1,3,6-naphthalenetrisulfonic acid, hexasodium salt.

* * * * *